(12) United States Patent
Hauser et al.

(10) Patent No.: US 10,105,454 B2
(45) Date of Patent: Oct. 23, 2018

(54) ULTRASHORT PEPTIDES AS EXOGENOUS SECOND HARMONIC PROBES FOR BIOIMAGING APPLICATIONS

(71) Applicant: Agency for Science, Technology and Research, Singapore (SG)

(72) Inventors: Charlotte Hauser, Singapore (SG); Ming Ni, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 19 days.

(21) Appl. No.: 15/324,144

(22) PCT Filed: Jul. 8, 2015

(86) PCT No.: PCT/SG2015/050204
§ 371 (c)(1),
(2) Date: Jan. 5, 2017

(87) PCT Pub. No.: WO2016/007091
PCT Pub. Date: Jan. 14, 2016

(65) Prior Publication Data
US 2017/0196993 A1 Jul. 13, 2017
US 2018/0036432 A9 Feb. 8, 2018

(30) Foreign Application Priority Data
Jul. 8, 2014 (SG) .......................... 10201403924Q

(51) Int. Cl.
| | |
|---|---|
| *A61K 49/00* | (2006.01) |
| *A61L 26/00* | (2006.01) |
| *C12Q 1/02* | (2006.01) |
| *A61L 27/52* | (2006.01) |
| *A61K 9/14* | (2006.01) |
| *A61K 47/42* | (2017.01) |
| *A61L 27/22* | (2006.01) |

(52) U.S. Cl.
CPC ................ *A61K 49/00* (2013.01); *A61K 9/14* (2013.01); *A61K 47/42* (2013.01); *A61L 26/008* (2013.01); *A61L 26/0047* (2013.01); *A61L 27/227* (2013.01); *A61L 27/52* (2013.01); *C12Q 1/02* (2013.01)

(58) Field of Classification Search
CPC .......... A61K 47/42; A61K 49/00; A61K 9/14; A61L 26/0047; A61L 26/008; A61L 27/227; A61L 27/52; C12Q 1/02
See application file for complete search history.

(56) References Cited

FOREIGN PATENT DOCUMENTS

| WO | WO 2014/104981 A1 | 7/2014 |
|---|---|---|
| WO | WO 2016/007091 A1 | 1/2016 |

OTHER PUBLICATIONS

Su et al. Determination of Collagen Nanostructure from Second-Order Susceptibility Tensor Analysis. Biophysical Journal, 2011. vol. 100, pp. 2053-2062. (Year: 2011).*
International Search Report and Written Opinion dated Sep. 16, 2015 in connection with International Application No. PCT/SG2015/050204.
International Preliminary Report on Patentability dated Jan. 19, 2017 in connection with International Application No. PCT/SG2015/050204.
Loison et al., Additive Model for the Second Harmonic Generation Hyperpolarizability Applied to a Collagen-Mimicking Peptide (Pro-Pro-Gly)$_{10}$. J. Phys. Chem. A. 2010;114(29):7769-79.

* cited by examiner

*Primary Examiner* — Marcela M Cordero Garcia
(74) *Attorney, Agent, or Firm* — Wolf, Greenfield & Sacks, P.C.

(57) ABSTRACT

Various aspects of the present invention relate to a peptide based biomaterial for visualization by SHG microscopy. In particular the invention relates to the use of short peptides as a non-linear optical (NLO) material for second harmonic generation (SHG) microscopy. A preferred short peptide comprises LIVAGK (LK6) and contains a non-polar aliphatic tail (with decreasing hydrophobicity) and a polar head; and can self-assemble into hydrogels; wherein which the peptide forms a tunable fibrous structure for in vitro and in vivo imaging applications and is suitable in disease diagnostics such as amyloidosis, including 1) neuro-degenerative amyloidosis, e.g. Alzheimer's (AD), Parkinson's, Huntington's (PD), 2) non-neuropathic localized amyloidosis such as in Type II Diabetes, and 3) systemic amyloidosis that occurs in multiple tissues, e.g. cataracts and lattice corneal dystrophy (LCD), as well as drug delivery and/or wound dressings.

19 Claims, 7 Drawing Sheets
Specification includes a Sequence Listing.

SEQUENCE LISTING

```
<160> NUMBER OF SEQ ID NOS: 102

<210> SEQ ID NO 1
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 1

Leu Ile Val Ala Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 2

Ile Leu Val Ala Gly
1               5
```

-continued

```
<210> SEQ ID NO 3
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 3

Ile Leu Val Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 4

Leu Ile Val Ala Ala
1               5

<210> SEQ ID NO 5
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 5

Leu Ala Val Ala Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 6

Ile Ala Val Ala Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 7

Ala Ile Val Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 8

Gly Ile Val Ala Gly
1               5

<210> SEQ ID NO 9
```

```
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 9

Val Ile Val Ala Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 10

Ala Leu Val Ala Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 11

Gly Leu Val Ala Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Aliphatic aa sequence of ultrashort peptide

<400> SEQUENCE: 12

Val Leu Val Ala Gly
1               5

<210> SEQ ID NO 13
<211> LENGTH: 4
<212> TYPE: PRT
<213> ORGANISM: Artificial Sequence
<220> FEATURE:
<223> OTHER INFORMATION: Aliphatic aa sequence of ultrashort peptide

<400> SEQUENCE: 13

Ile Val Ala Gly
1

<210> SEQ ID NO 14
<211> LENGTH: 4
<212> TYPE: PRT
<213> ORGANISM: Artificial Sequence
<220> FEATURE:
<223> OTHER INFORMATION: Aliphatic aa sequence of ultrashort peptide

<400> SEQUENCE: 14

Leu Ile Val Ala
1

<210> SEQ ID NO 15
<211> LENGTH: 4
```

```
<212> TYPE: PRT
<213> ORGANISM: Artificial Sequence
<220> FEATURE:
<223> OTHER INFORMATION: Aliphatic aa sequence of ultrashort peptide

<400> SEQUENCE: 15

Leu Ile Val Gly
1

<210> SEQ ID NO 16
<211> LENGTH: 4
<212> TYPE: PRT
<213> ORGANISM: Artificial Sequence
<220> FEATURE:
<223> OTHER INFORMATION: Aliphatic aa sequence of ultrashort peptide

<400> SEQUENCE: 16

Ile Leu Val Ala
1

<210> SEQ ID NO 17
<211> LENGTH: 4
<212> TYPE: PRT
<213> ORGANISM: Artificial Sequence
<220> FEATURE:
<223> OTHER INFORMATION: Aliphatic aa sequence of ultrashort peptide

<400> SEQUENCE: 17

Ile Leu Val Gly
1

<210> SEQ ID NO 18
<211> LENGTH: 4
<212> TYPE: PRT
<213> ORGANISM: Artificial Sequence
<220> FEATURE:
<223> OTHER INFORMATION: Aliphatic aa sequence of ultrashort peptide

<400> SEQUENCE: 18

Leu Val Ala Gly
1

<210> SEQ ID NO 19
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 19

Leu Ile Val Ala Gly Asp
1               5

<210> SEQ ID NO 20
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 20

Ile Leu Val Ala Gly Asp
1               5

<210> SEQ ID NO 21
<211> LENGTH: 6
<212> TYPE: PRT
```

```
<213> ORGANISM: Artificial Sequence
<220> FEATURE:
<223> OTHER INFORMATION: Ultrashort peptide

<400> SEQUENCE: 21

Ile Leu Val Ala Ala Asp
1               5

<210> SEQ ID NO 22
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 22

Leu Ile Val Ala Ala Asp
1               5

<210> SEQ ID NO 23
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 23

Leu Ala Val Ala Gly Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 24

Ile Ala Val Ala Gly Asp
1               5

<210> SEQ ID NO 25
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 25

Ala Ile Val Ala Gly Asp
1               5

<210> SEQ ID NO 26
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 26

Leu Ile Val Ala Gly Glu
1               5

<210> SEQ ID NO 27
<211> LENGTH: 6
<212> TYPE: PRT
<213> ORGANISM: Artificial Sequence
```

```
<220> FEATURE:
<223> OTHER INFORMATION: Ultrashort peptide

<400> SEQUENCE: 27

Leu Ile Val Ala Gly Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 28

Ile Leu Val Ala Gly Lys
1               5

<210> SEQ ID NO 29
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 29

Ile Leu Val Ala Ala Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 30

Ile Ala Val Ala Gly Lys
1               5

<210> SEQ ID NO 31
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 31

Ala Ile Val Ala Gly Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 32

Leu Ile Val Ala Gly Thr
1               5

<210> SEQ ID NO 33
<211> LENGTH: 6
<212> TYPE: PRT
<213> ORGANISM: Artificial Sequence
<220> FEATURE:
```

```
<223> OTHER INFORMATION: Ultrashort peptide

<400> SEQUENCE: 33

Ile Leu Val Ala Ala Thr
1               5

<210> SEQ ID NO 34
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 34

Ile Ala Val Ala Gly Thr
1               5

<210> SEQ ID NO 35
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 35

Ala Ile Val Ala Gly Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Ultrashort peptide

<400> SEQUENCE: 36

Leu Ile Val Ala Asp
1               5

<210> SEQ ID NO 37
<211> LENGTH: 5
<212> TYPE: PRT
<213> ORGANISM: Artificial Sequence
<220> FEATURE:
<223> OTHER INFORMATION: Ultrashort peptide

<400> SEQUENCE: 37

Leu Ile Val Gly Asp
1               5

<210> SEQ ID NO 38
<211> LENGTH: 5
<212> TYPE: PRT
<213> ORGANISM: Artificial Sequence
<220> FEATURE:
<223> OTHER INFORMATION: Ultrashort peptide

<400> SEQUENCE: 38

Ile Leu Val Ala Asp
1               5

<210> SEQ ID NO 39
<211> LENGTH: 5
<212> TYPE: PRT
<213> ORGANISM: Artificial Sequence
<220> FEATURE:
<223> OTHER INFORMATION: Ultrashort peptide
```

<400> SEQUENCE: 39

Ile Leu Val Gly Asp
1               5

<210> SEQ ID NO 40
<211> LENGTH: 5
<212> TYPE: PRT
<213> ORGANISM: Artificial Sequence
<220> FEATURE:
<223> OTHER INFORMATION: Ultrashort peptide

<400> SEQUENCE: 40

Leu Val Ala Gly Asp
1               5

<210> SEQ ID NO 41
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 41

Ile Val Ala Asp
1

<210> SEQ ID NO 42
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 42

Ile Val Ala Lys
1

<210> SEQ ID NO 43
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 43

Ile Val Gly Asp
1

<210> SEQ ID NO 44
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 44

Val Ile Gly Asp
1

<210> SEQ ID NO 45
<211> LENGTH: 4
<212> TYPE: PRT
<213> ORGANISM: Artificial Sequence
<220> FEATURE:
<223> OTHER INFORMATION: Ultrashort peptide

```
<400> SEQUENCE: 45

Ile Val Ala Asp
1

<210> SEQ ID NO 46
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 46

Val Ile Ala Asp
1

<210> SEQ ID NO 47
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 47

Ile Val Gly Lys
1

<210> SEQ ID NO 48
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 48

Val Ile Gly Lys
1

<210> SEQ ID NO 49
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 49

Ile Val Ala Lys
1

<210> SEQ ID NO 50
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 50

Val Ile Ala Lys
1

<210> SEQ ID NO 51
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 51
```

```
Ile Ile Ile Asp
1

<210> SEQ ID NO 52
<211> LENGTH: 4
<212> TYPE: PRT
<213> ORGANISM: Artificial Sequence
<220> FEATURE:
<223> OTHER INFORMATION: Ultrashort peptide

<400> SEQUENCE: 52

Ile Ile Ile Lys
1

<210> SEQ ID NO 53
<211> LENGTH: 6
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 53

Leu Ile Val Ala Gly Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 54

Ile Leu Val Ala Gly Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 55

Ile Leu Val Ala Ala Xaa
1               5

<210> SEQ ID NO 56
<211> LENGTH: 6
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 56

Ile Leu Val Ala Gly Xaa
1               5

<210> SEQ ID NO 57
<211> LENGTH: 5
<212> TYPE: PRT
<213> ORGANISM: Artificial Sequence
<220> FEATURE:
<223> OTHER INFORMATION: Ultrashort peptide with X = ornithine (Orn)

<400> SEQUENCE: 57

Ala Ile Val Ala Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 58

Leu Ile Val Ala Gly Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 59

Ile Leu Val Ala Gly Xaa
1               5

<210> SEQ ID NO 60
<211> LENGTH: 6
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 60

Ile Leu Val Ala Ala Xaa
1               5

<210> SEQ ID NO 61
<211> LENGTH: 6
<212> TYPE: PRT
<213> ORGANISM: Artificial Sequence
<220> FEATURE:
```

```
<223> OTHER INFORMATION: Ultrashort peptide with X = 2,4-diaminobutyric
      acid (Dab)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 61

Ile Ala Val Ala Gly Xaa
1               5

<210> SEQ ID NO 62
<211> LENGTH: 6
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 62

Ala Ile Val Ala Gly Xaa
1               5

<210> SEQ ID NO 63
<211> LENGTH: 6
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 63

Leu Ile Val Ala Gly Xaa
1               5

<210> SEQ ID NO 64
<211> LENGTH: 6
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 64

Ile Leu Val Ala Gly Xaa
1               5

<210> SEQ ID NO 65
<211> LENGTH: 6
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 65

Ile Leu Val Ala Ala Xaa
1               5

<210> SEQ ID NO 66
<211> LENGTH: 6
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 66

Ile Ala Val Ala Gly Xaa
1               5

<210> SEQ ID NO 67
<211> LENGTH: 6
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (6)..(6)
<223> OTHER INFORMATION: Xaa can be any naturally occurring amino acid

<400> SEQUENCE: 67

Ala Ile Val Ala Gly Xaa
1               5

<210> SEQ ID NO 68
<211> LENGTH: 5
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 68

Leu Ile Val Ala Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 69

Leu Ile Val Gly Xaa
1               5

<210> SEQ ID NO 70
<211> LENGTH: 5
<212> TYPE: PRT
```

```
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 70

Ile Leu Val Ala Xaa
1               5

<210> SEQ ID NO 71
<211> LENGTH: 5
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 71

Ile Leu Val Gly Xaa
1               5

<210> SEQ ID NO 72
<211> LENGTH: 5
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 72

Leu Val Ala Gly Xaa
1               5

<210> SEQ ID NO 73
<211> LENGTH: 5
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 73

Leu Ile Val Ala Xaa
1               5

<210> SEQ ID NO 74
<211> LENGTH: 5
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 74
```

```
Leu Ile Val Gly Xaa
1               5

<210> SEQ ID NO 75
<211> LENGTH: 5
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 75

Ile Leu Val Ala Xaa
1               5

<210> SEQ ID NO 76
<211> LENGTH: 5
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 76

Ile Leu Val Gly Xaa
1               5

<210> SEQ ID NO 77
<211> LENGTH: 5
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 77

Leu Val Ala Gly Xaa
1               5

<210> SEQ ID NO 78
<211> LENGTH: 5
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 78

Leu Ile Val Ala Xaa
1               5

<210> SEQ ID NO 79
<211> LENGTH: 5
```

```
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 79

Leu Ile Val Gly Xaa
1               5

<210> SEQ ID NO 80
<211> LENGTH: 5
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 80

Ile Leu Val Ala Xaa
1               5

<210> SEQ ID NO 81
<211> LENGTH: 5
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 81

Ile Leu Val Gly Xaa
1               5

<210> SEQ ID NO 82
<211> LENGTH: 5
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (5)..(5)
<223> OTHER INFORMATION: Xaa can be any naturally occurring amino acid

<400> SEQUENCE: 82

Leu Val Ala Gly Xaa
1               5

<210> SEQ ID NO 83
<211> LENGTH: 4
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (4)..(4)
```

<223> OTHER INFORMATION: Xaa can be any naturally occurring amino acid

<400> SEQUENCE: 83

Ile Val Ala Xaa
1

<210> SEQ ID NO 84
<211> LENGTH: 4
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 84

Ile Val Gly Xaa
1

<210> SEQ ID NO 85
<211> LENGTH: 4
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 85

Val Ile Gly Xaa
1

<210> SEQ ID NO 86
<211> LENGTH: 4
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 86

Ile Val Ala Xaa
1

<210> SEQ ID NO 87
<211> LENGTH: 4
<212> TYPE: PRT
<213> ORGANISM: Artificial Sequence
<220> FEATURE:
<223> OTHER INFORMATION: Ultrashort peptide with X = ornithine (Orn)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 87

Val Ile Ala Xaa
1

<210> SEQ ID NO 88
<211> LENGTH: 4
<212> TYPE: PRT

```
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 88

Ile Val Ala Xaa
1

<210> SEQ ID NO 89
<211> LENGTH: 4
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 89

Ile Val Gly Xaa
1

<210> SEQ ID NO 90
<211> LENGTH: 4
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 90

Val Ile Gly Xaa
1

<210> SEQ ID NO 91
<211> LENGTH: 4
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

Ile Val Ala Xaa
1

<210> SEQ ID NO 92
<211> LENGTH: 4
<212> TYPE: PRT
<213> ORGANISM: Artificial Sequence
<220> FEATURE:
<223> OTHER INFORMATION: Ultrashort peptide with X = 2,4-diaminobutyric
      acid (Dab)
<220> FEATURE:
<221> NAME/KEY: misc_feature
<222> LOCATION: (4)..(4)
```

<223> OTHER INFORMATION: Xaa can be any naturally occurring amino acid

<400> SEQUENCE: 92

Val Ile Ala Xaa
1

<210> SEQ ID NO 93
<211> LENGTH: 4
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 93

Ile Val Ala Xaa
1

<210> SEQ ID NO 94
<211> LENGTH: 4
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 94

Ile Val Gly Xaa
1

<210> SEQ ID NO 95
<211> LENGTH: 4
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 95

Val Ile Gly Xaa
1

<210> SEQ ID NO 96
<211> LENGTH: 4
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 96

Ile Val Ala Xaa
1

```
<210> SEQ ID NO 97
<211> LENGTH: 4
<212> TYPE: PRT
<213> ORGANISM: Artificial Sequence
<220> FEATURE:
<223> OTHER INFORMATION: Ultrashort peptide with X = 2,3-
      diaminopropionic acid (Dap)
<220> FEATURE:
<221> NAME/KEY: misc_feature
<222> LOCATION: (4)..(4)
<223> OTHER INFORMATION: Xaa can be any naturally occurring amino acid

<400> SEQUENCE: 97

Val Ile Ala Xaa
1

<210> SEQ ID NO 98
<211> LENGTH: 6
<212> TYPE: PRT
<213> ORGANISM: Artificial Sequence
<220> FEATURE:
<223> OTHER INFORMATION: Ultrashort peptide

<400> SEQUENCE: 98

Ile Leu Val Ala Gly Ser
1               5

<210> SEQ ID NO 99
<211> LENGTH: 7
<212> TYPE: PRT
<213> ORGANISM: Homo sapiens

<400> SEQUENCE: 99

Lys Leu Val Phe Phe Ala Glu
1               5

<210> SEQ ID NO 100
<211> LENGTH: 6
<212> TYPE: PRT
<213> ORGANISM: Homo sapiens

<400> SEQUENCE: 100

Gly Gly Val Val Ile Ala
1               5

<210> SEQ ID NO 101
<211> LENGTH: 5
<212> TYPE: PRT
<213> ORGANISM: Homo sapiens

<400> SEQUENCE: 101

Asp Phe Asn Lys Phe
1               5

<210> SEQ ID NO 102
<211> LENGTH: 6
<212> TYPE: PRT
<213> ORGANISM: Homo sapiens

<400> SEQUENCE: 102

Asn Phe Gly Ala Ile Leu
1               5
```

ULTRASHORT PEPTIDES AS EXOGENOUS SECOND HARMONIC PROBES FOR BIOIMAGING APPLICATIONS

CROSS REFERENCE TO RELATED APPLICATIONS

This application is the U.S. National Stage, pursuant to 35 U.S.C. § 371, of U.S. International Application No. PCT/SG2015/050204, filed Jul. 8, 2015, designating the United States and published on Jan. 14, 2016 as Publication WO 2016/007091 A1, which claims the benefit of Singapore Patent Application No. 10201403924Q filed Jul. 8, 2014, which applications are expressly incorporated by reference herein.

FIELD OF INVENTION

The present invention is in the area of biodevices and diagnostics. The invention generally relates to second harmonic generation (SHG) microscopy for disease diagnosis and envisioning of tissue engineering scaffolds.

BACKGROUND

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Second harmonic generation (SHG) microscopy is a powerful imaging tool for disease diagnosis and envision of tissue engineering scaffolds. Second harmonic (SH) probes have been developed for in-vivo imaging in recent years as they possess many advantages over the classic fluorescent probes. SH probes are typically made of inorganic nanomaterials, such as barium titanate nanocrystals. Although these materials have achieved certain success in molecular imaging, they are concerned for their health and environmental issues.

In addition, second-harmonic generation (SHG) microscopy is a nonlinear optical (NLO) imaging technique that has emerged in recent years to visualize structures or functions of cells, tissues and organisms [1]. It has the advantages of being label-free, inherent three-dimensional (3D) resolution, near-infrared (NIR) excitation for superior optical penetration, lower photo-damage, and capable of providing quantitative information, which makes it an attractive tool for high resolution imaging [1-3]. It has been used to diagnose a wide range of diseases including cancer, liver fibrosis and skin damage [4]. It has also been used in tissue engineering and regenerative medicine [5] to envision three-dimensional biomaterial scaffolds and extracellular matrices that secreted by cells [6-7].

SHG is an optical frequency doubling process: when a non-linear optical (NLO) material interacts with light, two NIR incident photons can be converted into one emerging visible photon at exactly twice the energy (or half the wavelength) [1,4,9]. This NLO material requires a noncentrosymmetric structure. Examples include potassium niobate (KNbO3), lithium niobate (LiNbO3), barium titanate (BaTiO3), potassium titanyl phosphate (KTiOPO4, KTP), and zinc oxide (ZnO), Gallium nitride (GaN), Silicon carbide (SiC), noble metal particles, and quantum dots [8,9].

Inorganic nanomaterials, such as BaTiO3 nanocrsytal has been used a second harmonic (SH) probe for in vivo imaging [13]. These SHG nanoprobes are superior to the existing fluorescent dyes in terms of dye bleaching, signal saturation and narrow emission spectrum (full width at half maximum (FWHM)<5 nm) [13, 14]. Although a report showed that BaTiO3 nanocrsytals are non-toxic to zebrafish [13], inorganic nanomaterials have been questioned for their health and environmental issues which enormously limit their clinical applications [15-16].

SUMMARY

The present invention provides a peptide based biomaterial for visualization by SHG microscopy. The present invention comprises the following features:

F1) Use of short peptides as a non-linear optical (NLO) material for second harmonic generation (SHG) microscopy.

F2) A preferred peptide of F1 is LIVAGK (LK6) (SEQ ID NO: 27), which contains a non-polar aliphatic tail (with decreasing hydrophobicity) and a polar head; and can self-assemble into hydrogels;

A. Wherein the peptide forms a tunable fibrous structure

B. For in vitro and in vivo imaging applications

C. In disease diagnostics such as amyloidosis, including 1) neuro-degenerative amyloidosis, e.g. Alzheimer's (AD), Parkinson's, Huntington's (PD), 2) non-neuropathic localized amyloidosis such as in Type II Diabetes, and 3) systemic amyloidosis that occurs in multiple tissues, e.g. cataracts and lattice corneal dystrophy (LCD). In accordance with an aspect of the invention, the invention provides the use of a peptide and/or peptidomimetic, capable of self-assembling and forming a hydrogel, having the general formula I:

$$Z_a\text{-}(X)_b\text{-}(Y)_c\text{-}Z'_d \qquad (I)$$

wherein

Z is an N-terminal protecting group;

a is 0 or 1, preferably 1;

X is, at each occurrence, independently selected from the group consisting of aliphatic amino acids and aliphatic amino acid derivatives, and wherein the overall hydrophobicity decreases from N- to C-terminus;

b is an integer selected from 1 to 7;

Y is selected from the group consisting of polar amino acids and polar amino acid derivatives;

c is 1 or 2;

Z' is a C-terminal protecting group; and d is 0 or 1, and b+c is at least 2, as a non-linear optical (NLO) material for second harmonic generation (SHG) microscopy and/or imaging.

Preferably, said aliphatic amino acids and aliphatic amino acid derivatives, and said polar amino acids and polar amino acid derivatives are either D-amino acids or L-amino acids.

Preferably, said aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), preferably from the group consisting of alanine (Ala, A), isoleucine (Ile, I), leucine (Leu, L), valine (Val, V) and glycine (Gly, G).

Preferably, all or a portion of said aliphatic amino acids are arranged in an order of decreasing amino acid size in the direction from N- to C-terminus, wherein the size of the aliphatic amino acids is defined as I=L>V>A>G.

Preferably, said aliphatic amino acids have a sequence selected from
LIVAG (SEQ ID NO: 1),
ILVAG (SEQ ID NO: 2),
ILVAA (SEQ ID NO: 3),
LIVAA (SEQ ID NO: 4),
LAVAG (SEQ ID NO: 5),
IAVAG (SEQ ID NO: 6),
AIVAG (SEQ ID NO: 7),
GIVAG (SEQ ID NO: 8),
VIVAG (SEQ ID NO: 9),
ALVAG (SEQ ID NO: 10),
GLVAG (SEQ ID NO: 11),
VLVAG (SEQ ID NO: 12),
IVAG (SEQ ID NO: 13),
LIVA (SEQ ID NO: 14),
LIVG (SEQ ID NO: 15),
ILVA (SEQ ID NO: 16),
ILVG (SEQ ID NO: 17),
LVAG (SEQ ID NO: 18),
VA
IVG,
VIG,
WA,
VIA,
IV and
VI.

Preferably, b is an integer from 2 to 7 or 2 to 6.

Preferably, said polar amino acids are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, threonine (Thr, T), allothreonine, serine (Ser, S), homoserine, arginine (Arg, R), homoarginine, ornithine (Orn), lysine (Lys, K), N(6)-carboxymethyllysine, histidine (His, H), 2,4-diaminobutyric acid (Dab), 2,3-diaminopropionic acid (Dap), and N(6)-carboxymethyllysine, wherein said polar amino acid is preferably selected from the group consisting of aspartic acid, asparagine, glutamic acid, glutamine, serine, threonine, methionine, lysine, ornithine (Orn), 2,4-diaminobutyric acid (Dab), and 2,3-diaminopropionic acid (Dap).

Preferably, c is 2 and said polar amino acids are identical amino acids, or wherein c is 1 and said polar polar amino acid comprises any one of aspartic acid, asparagine, glutamic acid, glutamine, serine, threonine, cysteine, methionine, lysine, ornithine, 2,4-diaminobutyric acid (Dab) and histidine, preferably lysine, ornithine, 2,4-diaminobutyric acid (Dab) and 2,3-diaminopropionic acid (Dap).

Preferably, $(Y)_b$ has a sequence selected from Asp, Asn, Glu, Gln, Ser, Thr, Cys, Met, Lys, Orn, Dab, His, Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu, Cys-Asp, Cys-Lys, Cys-Ser, Cys-Thr, Cys-Orn, Cys-Dab, Cys-Dap, Lys-Lys, Lys-Ser, Lys-Thr, Lys-Orn, Lys-Dab, Lys-Dap, Ser-Lys, Ser-Orn, Ser-Dab, Ser-Dap, Orn-Lys, Orn-Orn, Orn-Ser, Orn-Thr, Orn-Dab, Orn-Dap, Dab-Lys, Dab-Ser, Dab-Thr, Dab-Orn, Dab-Dab, Dab-Dap, Dap-Lys, Dap-Ser, Dap-Thr, Dap-Orn, Dap-Dab, Dap-Dap.

Preferably, $(X)_a$-$(Y)_b$ has a sequence selected from the group consisting of
LIVAGD (SEQ ID NO: 19),
ILVAGD (SEQ ID NO: 20),
ILVAAD (SEQ ID NO: 21),
LIVAAD (SEQ ID NO: 22),
LAVAGD (SEQ ID NO: 23),
IAVAGD (SEQ ID NO: 24),
AIVAGD (SEQ ID NO: 25),
LIVAGE (SEQ ID NO: 26),
LIVAGK (SEQ ID NO: 27),
ILVAGK (SEQ ID NO. 28),
ILVAAK (SEQ ID NO: 29),
IAVAGK (SEQ ID NO: 30),
AIVAGK (SEQ ID NO: 31),
LIVAGT (SEQ ID NO: 32),
ILVAAT (SEQ ID NO: 33),
IAVAGT (SEQ ID NO: 34),
AIVAGT (SEQ ID NO: 35),
LIVAD (SEQ ID NO: 36),
LIVGD (SEQ ID NO: 37),
ILVAD (SEQ ID NO: 38),
ILVGD (SEQ ID NO: 39),
LVAGD (SEQ ID NO: 40),
IVAD (SEQ ID NO: 41),
IVAK (SEQ ID NO: 42),
IVGD (SEQ ID NO: 43),
VIGD (SEQ ID NO: 44),
IVAD (SEQ ID NO: 45),
VIAD (SEQ ID NO: 46),
IVGK (SEQ ID NO: 47),
VIGK (SEQ ID NO: 48),
IVAK (SEQ ID NO: 49),
VIAK (SEQ ID NO: 50),
IIID (SEQ ID NO: 51),
IIIK (SEQ ID NO: 52),
IVD,
IVK,
IID,
LVE,
IVE,
LVD,
VIE,
VID,
VIK,
VLD,
VLE,
LLE,
LLD,
IIE,
ID,
IE,
LIVAGOrn (SEQ ID NO: 53),
ILVAGOrn (SEQ ID NO: 54),
ILVAAOrn (SEQ ID NO: 55),
IAVAGOrn (SEQ ID NO: 56),
AIVAGOrn (SEQ ID NO: 57),
LIVAGDab (SEQ ID NO: 58),
ILVAGDab (SEQ ID NO: 59),
ILVAADab (SEQ ID NO: 60),
IAVAGDab (SEQ ID NO: 61),
AIVAGDab (SEQ ID NO: 62),
LIVAGDap (SEQ ID NO: 63),
ILVAGDap (SEQ ID NO: 64),
ILVAADap (SEQ ID NO: 65),
IAVAGDap (SEQ ID NO: 66),
AIVAGDap (SEQ ID NO: 67),
LIVAOrn (SEQ ID NO: 68),
LIVGOrn (SEQ ID NO: 69),
ILVAOrn (SEQ ID NO: 70), ILVGOrn (SEQ ID NO: 71),
LVAGOrn (SEQ ID NO: 72),
LIVADab (SEQ ID NO: 73),
LIVGDab (SEQ ID NO: 74),
ILVADab (SEQ ID NO: 75),
ILVGDab (SEQ ID NO: 76),
LVAGDab (SEQ ID NO: 77),
LIVADap (SEQ ID NO: 78),
LIVGDap (SEQ ID NO: 79),
ILVADap (SEQ ID NO: 80),
ILVGDap (SEQ ID NO: 81),
LVAGDap (SEQ ID NO: 82),
IVAOrn (SEQ ID NO: 83),
IVGOrn (SEQ ID NO: 84),
VIGOrn (SEQ ID NO: 85),
IVAOrn (SEQ ID NO: 86),
VIAOrn (SEQ ID NO: 87),
IVADab (SEQ ID NO: 88),
IVGDab (SEQ ID NO: 89),
VIGDab (SEQ ID NO: 90),
IVADab (SEQ ID NO: 91),
VIADab (SEQ ID NO: 92),
IVADap (SEQ ID NO: 93),
IVGDap (SEQ ID NO: 94),
VIGDap (SEQ ID NO: 95),
IVADap (SEQ ID NO: 96),
VIADap (SEQ ID NO: 97),
IVOrn,
IVDab,
IVDap,
VIOrn,
VIDab,
VIDap, and
ILVAGS (SEQ ID NO: 98).

In accordance with an aspect of the invention, the invention provides the use of a peptide having the general formula II:

$$Z_a\text{-M-}Z'_d \qquad (II)$$

wherein
Z is an N-terminal protecting group;
a is 0 or 1, preferably 1;
M is an amino acid sequence selected from SEQ ID Nos. 99 to 102;
Z' is a C-terminal protecting group; and
d is 0 or 1,
as a non-linear optical (NLO) material for second harmonic generation (SHG) microscopy and/or imaging.

The peptides with amino acid sequences selected from SEQ ID Nos. 99 to 102 are four natural amyloidogenic core sequences ($KE_7$, $GA_6$, $DF_5$, $NL_6$).

See below for further details, e.g. Table 1.

In both general formulas I and II:

Preferably, a is 1 and said N-terminal protecting group Z has the general formula —C(O)—R, wherein R is selected from the group consisting of H, unsubstituted or substituted alkyls, and unsubstituted or substituted aryls, wherein R is preferably selected from the group consisting of methyl, ethyl, propyl, isopropyl, butyl and isobutyl.

Preferably, said N-terminal protecting group Z is an acetyl group.

Preferably, said N-terminal protecting group Z is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

Preferably, said C-terminal protecting group Z' is an amide group, wherein, preferably, the C-terminus has the formula —CONHR or —CONRR', with R and R' being selected from the group consisting of H, unsubstituted or substituted alkyls, and unsubstituted or substituted aryls.

Preferably, said C-terminal protecting group Z' is an ester group, wherein, preferably, the C-terminus has the formula —$CO_2R$, with R being selected from the group consisting of H, unsubstituted or substituted alkyls, and unsubstituted or substituted aryls.

Preferably, said C-terminal group Z' is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

Preferably, b+c is at least 2, preferably 2 to 9, more preferably 3 to 7 or 2 to 7.

Preferably, the peptide and/or peptidomimetic is visualized under a second harmonic generation (SHG) microscopy or by SHG imaging without additional dye(s) and/or label(s).

Preferably, the peptide and/or peptidomimetic comprises further compound(s), such as
  small molecules,
    such as (but not limited to) sugars, alcohols, hydroxy acids, amino acids, vitamins, biotin, L-Dopa, thyroxine;
  bioactive molecules or moieties,
    such as growth factors, cytokines, lipids, cell receptor ligands, hormones, prodrugs, drugs, vitamins, antigens, antibodies, antibody fragments, oligonucleotides (including but not limited to DNA, messenger RNA, short hairpin RNA, small interfering RNA, microRNA, peptide nucleic acids, aptamers), saccharides;
  label(s), dye(s),
    such as imaging contrast agents;
  pathogens,
    such as viruses, bacteria and parasites;
  micro- and nanoparticles
  or combinations thereof
which are preferably covalently attached or coupled to the peptide and/or peptidomimetic, preferably to the C-terminal group Z', amino acid side chain(s) and/or linker,
wherein said attachment or coupling can be carried out before, during or after self-assembly of the peptide and/or peptidomimetic.

Preferably, the at least one peptide and/or peptidomimetic forms a fibrous structure, which is preferably tunable, such as
  in the way of peptide material's preparation (fiber structures, particle structures),
  for excitation wavelength tunability of SHG signals.

Preferably, the fibrous structure is a fibrous scaffold resembling the collagen fiber in extracellular matrix.

Preferably, the at least one peptide and/or peptidomimetic as defined herein is stable in aqueous solution at physiological conditions at ambient temperature for a period of time in the range from 1 day to at least 6 months, preferably to at least 8 months more preferably to at least 12 months.

Preferably the at least one peptide and/or peptidomimetic as defined herein is stable in aqueous solution at physiological conditions, at a temperature up to 90° C., for at least 1 hour.

Preferably, the peptide and/or peptidomimetic is present at a concentration in the range of from 0.1% to 30% (w/w), preferably 0.1% to 20% (w/w), more preferably 0.1% to 10% (w/w), more preferably 0.1% to 5% (w/w), even more preferably 0.1% to 3% (w/w), with respect to the total weight of said hydrogel or fibrous structure.

In accordance with another aspect of the invention there comprises a method of preparing a hydrogel or fibrous structure, the method comprising dissolving at least one peptide and/or peptidomimetic—as defined herein with general formula I—of the first aspect of the invention in an aqueous solution.

Preferably, the dissolved peptide and/or peptidomimetic in aqueous solution is further exposed to temperature, wherein the temperature is in the range from 20° C. to 90° C., preferably from 20° C. to 70° C.

Preferably, the at least one peptide and/or peptidomimetic is dissolved at a concentration from 0.01 µg/ml to 100 mg/ml, preferably at a concentration from 1 mg/ml to 50 mg/ml, more preferably at a concentration from about 1 mg/ml to about 20 mg/ml.

In accordance with another aspect of the invention, a method of preparing peptide particles is provided, the method comprising dissolving at least one peptide and/or peptidomimetic as defined herein with general formula I in an aqueous solution, preferably phosphate buffered saline (PBS), and solvent evaporation from said aqueous solution, such as by vacuum drying.

In another aspect of the invention, the invention provides a use according to the present invention or the use of a hydrogel, fibrous structure or peptide particle obtained by a method according to the present invention, as probes for (bio-)imaging, preferably as exogenous SHG probes.

In another aspect of the invention, the invention provides a use according to the present invention or the use of a hydrogel, fibrous structure or peptide particle obtained by a method according to the present invention, for monitoring cells, in vitro and/or in vivo (bio-)imaging.

In another aspect of the invention, there comprises a use according to the present invention or the use of a hydrogel, fibrous structure or peptide particle obtained by a method according to the present invention for visualizing peptide-based tissue engineering scaffolds, preferably comprising studying biological processes, such as cell adhesion, migration and differentiation.

In accordance with another aspect of the invention, the invention provides the use of a hydrogel, fibrous structure or peptide particle obtained by a method according the present invention as diagnostics, preferably for the diagnosis of diseases comprising or associated with the aggregation of peptide or protein structures, such as amyloidosis, including 1) neuro-degenerative amyloidosis, e.g. Alzheimer's (AD), Parkinson's, Huntington's (PD), 2) non-neuropathic localized amyloidosis such as in Type II Diabetes, and 3) systemic amyloidosis that occurs in multiple tissues, e.g. cataracts and lattice corneal dystrophy (LCD).

In another aspect of the invention, the invention provides the use of a hydrogel, fibrous structure or peptide particle obtained by a method according to the present invention as drug or gene delivery vehicle.

In another aspect of the invention, the invention provides a peptide particle comprising the peptide and/or peptidomimetic as defined herein, preferably obtained by a method of the present invention.

Preferably, the peptide particle has a particle size in the range from submicron to 10 microns.

In accordance with another aspect of the invention, the invention provides a drug or gene delivery vehicle comprising the peptide and/or peptidomimetic as defined herein, and a drug or gene to be delivered.

In accordance with another aspect of the invention, the invention provides a peptide-based tissue engineering scaffold comprising the peptide and/or peptidomimetic as defined herein, preferably obtained by a method according to the present invention.

In accordance with another aspect of the invention, the invention provides a biosensor or bioimaging device comprising the peptide and/or peptidomimetic as defined herein.

In accordance with another aspect of the invention, the invention provides a wound dressing comprising the peptide and/or peptidomimetic as defined herein.

Other aspects and features of the present invention will become apparent to those skilled in the art upon review of the following description of specific embodiments of the invention in conjunction with the accompanying figures.

BRIEF DESCRIPTION OF DRAWINGS

Embodiments of the invention will now be described by way of example with reference to the accompanying drawings.

(a) Comparison of the SHG signal intensity from endogenous collagen I (inset, in vivo SHG image of the normal capsular region of rat liver, left) to $LK_6$ peptide particles (inset, SHG image of $LK_6$ peptide particles, right). Instrument settings for both SHG imaging were the same. Five spots from each image were chosen and the SHG signal intensity was normalized to collagen I (mean±standard deviation, n=5);

SEM images of collagen fibers (b) and peptide particles (c).

Figure 2:
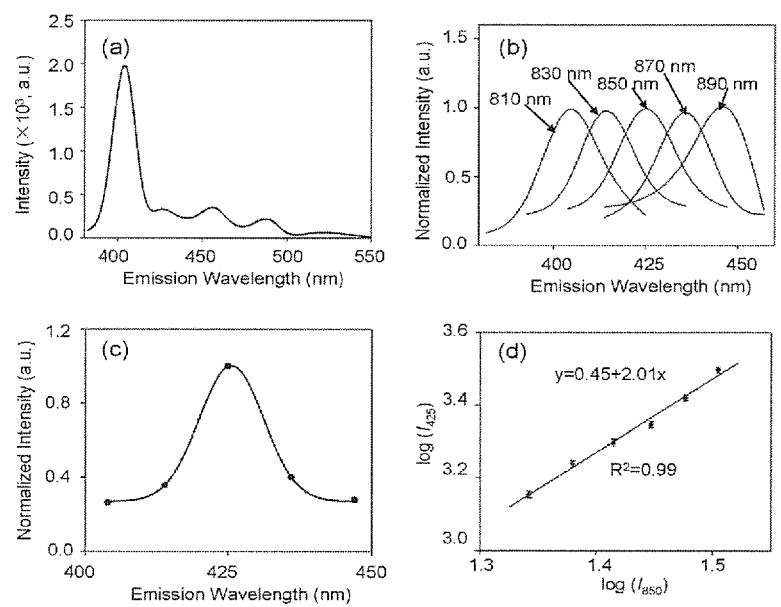

FIG. 2. $LK_6$ peptides are SHG active.

(a) SHG signal spectrum of $LK_6$ peptide. Signal was ranging from 380 to 550 nm with excitation wavelength of 810 nm and peak emission wavelength was shown at 405 nm.

(b) Spectral peaks at various excitation wavelengths spanning a broad spectral region (810-890 nm).

(c) Emission λ-scan of the SHG signal ($\lambda_{ex}$=850 nm) acquired from SHG imaging of $LK_6$ peptide particles. The solid spheres represent back scattering SHG data and the solid line represents a Gaussian fit. The full width at half-maximum of the fitted curve bears a $1/\sqrt{2}$ relation to the spectral profile of the corresponding beam.

(d) Log-log plot of the above SHG signal measurements demonstrating a log $[I_{425}]$=0.45+2.01×log $[I_{850}]$ dependence, quadratic to a good approximation, consistent with nonlinear second order optical upconversion.

Figure 3:
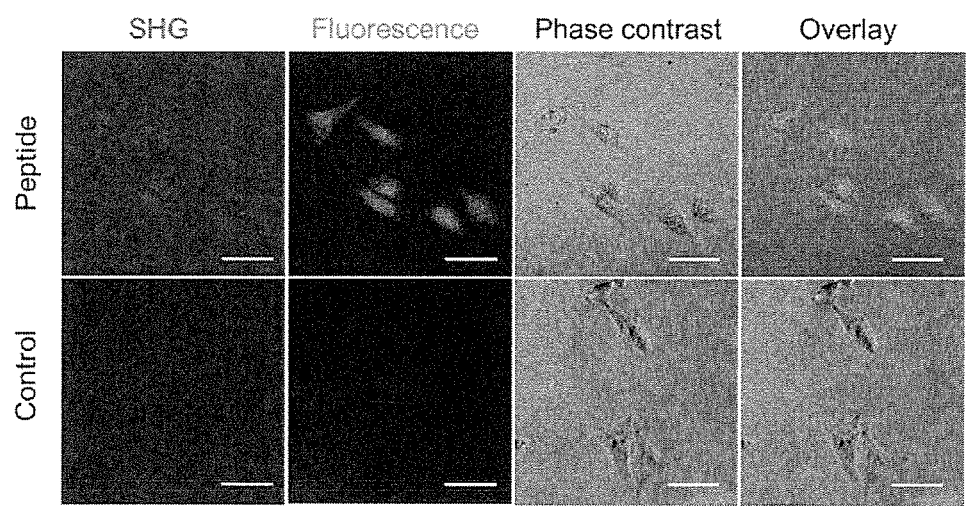

FIG. 3. Cellular uptake of biotin-conjugated $LK_6$.

Upper panel: HeLa cells exposed to biotin-conjugated $LK_6$ peptide containing medium. Peptides in HeLa cells displayed pseudo red color (SHG) and green color (fluorescence).

Lower panel: HeLa cells exposed to normal medium without peptide (control). Scale bars: 50 µm.

Figure 4:
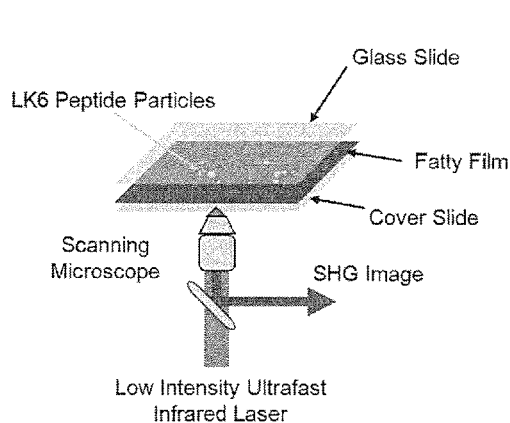
Figure 4:
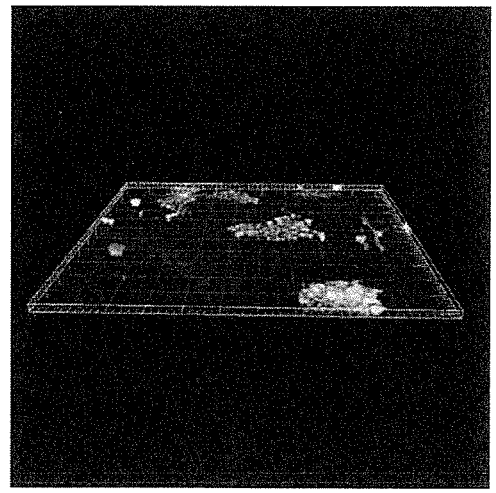

FIG. 4. Interface of $LK_6$ peptide particles and animal fat tissue.

(a) Schematic illustration of experiment arrangement: a low intensity ultrafast infrared laser penetrating glass cover slip and rat fat tissue (thickness~50 μm) and viewing $LK_6$ peptide particles sandwiched in between the glass slide and the glass cover slip.

(b) Three dimensional image of $LK_6$ peptide particles in the entire volume of (225×225×4.5 μm$^3$). SHG z-stack was generated with 0.5 μm step. Total nine images were taken (z=4.5 μm).

Figure 5:
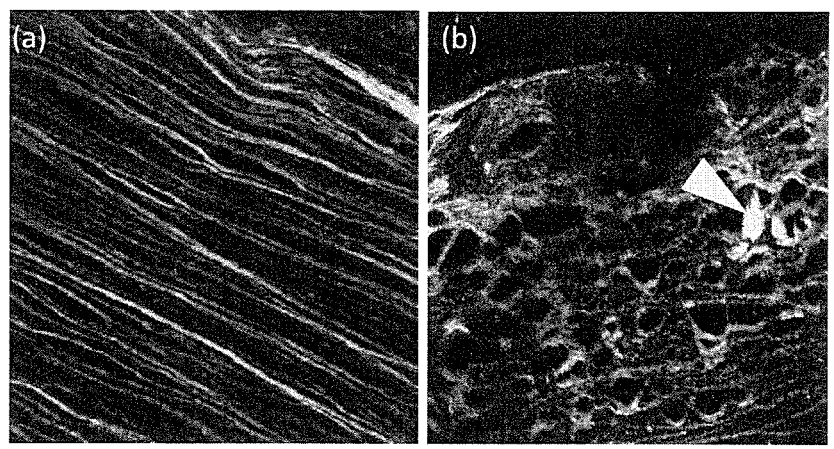

FIG. 5. SHG images of human corneal biopsy samples.

(a) Sample from a normal person (control; (b)) and a patient who has Lattice corneal dystrophy (LCD) disease. Collagen fibrils can be seen under SHG (green). Arrow indicates the amyloid deposit. Scale bar=20 μm.

Figure 6:
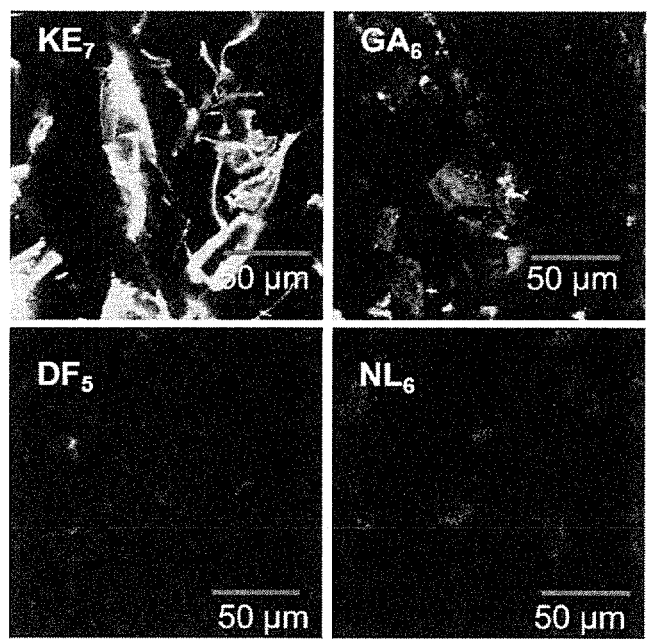

FIG. 6: SHG images of four pristine peptides with natural amyloidogenic core sequences.

The whole window was covered with pristine peptides. However, only part of the peptides can be visualized under SHG microscopy. The SHG intensity follows the order of $KE_7 > GA_6 > DF_5 > NL_6$. Scale bar=50 μm.

Figure 7:
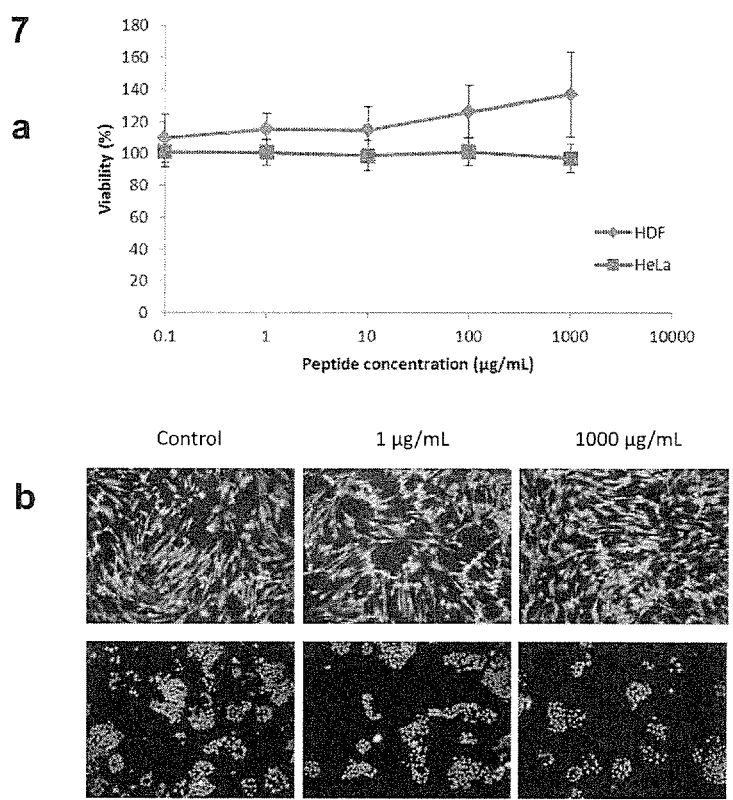

FIG. 7: Cytotoxicity studies of $LK_6$ peptide treated HDF and HeLa cells.

(a) Cell viability at 48 h of HDF and HeLa cells incubated with cell culture media containing $LK_6$ peptide solutions, as determined by the MTS assay (mean±standard deviation, n=9). Concentrations ranged from 0.1 to 1000 μg/mL.

(b) Cytotoxicity determined by Calcein AM/EthD-1 (live/dead, green/red) staining method after 48 h treated with 1 and 1000 μg/mL $LK_6$ peptide solutions using non-treated cells as control.

Scale bars: 100 μm.

Other arrangements of the invention are possible and, consequently, the accompanying drawings are not to be understood as superseding the generality of the preceding description of the invention.

DETAILED DESCRIPTION

Peptide/protein based biomaterials can also be assembled into large, ordered noncentrosymmetric structures, which make them possible to produce second harmonic signals [1]. Famous example include collagen I [10], diphenylalanine (FF, a dimer peptide) [11], elastin and muscle myosin [12]. Among them, collagen I has been commonly used as an endogenous SHG probe for disease diagnosis [4].

Peptide/protein based biomaterials appear to be a promising candidate for a SH probe due to their biocompatibility and biodegradability. A peptide-based biomaterial, i.e. a ultrashort peptide biomaterial is presented that can be directly visualized by second harmonic generation microscopy. It shows excitation wavelength tenability, similar second harmonic signal intensity as endogeneous collagen I, and cytocompatibility with two human cell lines.

Based on the above, the inventors concluded that the purely synthetic, peptide-based material holds the potential to be used as a future SH probe for bioimaging applications. In particular the Supramolecular assembly of collagen in tissues has been visualized by SHG microscopy for more than a decade. It was discovered by the inventors that striking similarity exists between ultrashort peptides and collagen fibers. Inspired by such findings, the non-linear optical (NLO) properties of a hexemer peptide, Ac-LIVAGK-NH2 (LK6) (SEQ ID NO: 27) was investigated.

A hexamer peptide Ac-LIVAGK-NH$_2$ (LK6) (SEQ ID NO: 27) was designed and synthesized. This hexamer peptide can self-assemble into hydrogels through hydrophobic interactions, ionic interactions, hydrogen bonding and van de Waals forces. It contains a non-polar aliphatic tail and a polar head. The non-polar aliphatic tail was designed to have a decreasing hydrophobicity. This type of arrangement favours a parallel-antiparallel stacking. The nanostructured peptide aggregates then form a fibrous scaffold, which resembles the collagen fiber in extracellular matrix [17-18]. In this work, the ultrashort peptide is submitted as a novel NLO material for SHG imaging. Results suggest this purely synthetic, peptide-based material holds the potential to be used as a future SH probe for bioimaging applications.

Supramolecular assembly of collagen in tissues has been visualized by SHG microscopy for more than a decade [4]. In particular, collagen I (in blood vessels, bone, cornea, kidney, liver, lung, ovary, skin and tendon), and collagen II (in cartilage) have been found to efficiently produce SHG [4]. Since diseased and normal tissues show different distribution patterns of collagen fiber alignment and intensity, their SHG images can be used for disease diagnosis.

Success has been achieved in many clinical applications, for example cancer delineation and liver fibrosis [4]. Collagen is a triple-helix molecule and can self-assemble into fibers with diameters up to a few micrometers. A recent study [19] showed that the origin of SHG signals from collagen fibers possibly lies in their peptide bonds. The building blocks of collagen fiber were mimicked by tri-amino acid peptides PPG and GGG (P and G are the one letter code for Proline and Glycine respectively) and a molecular-level property of the nonlinearity, i.e., the first hyperpolarizability, β, was measured by Hyper Rayleigh Scattering (HRS). The first hyperpolarizability of these trimers was about 0.087×10-30 esu (esu is the unit of the first hyperpolarizability) [19]. However, the first hyperpolarizability of collagen I was found to be (1250±20)×10-30 esu [19], which could be viewed as ten thousand trimers combining together.

Previous studies from our lab showed striking similarity between the ultrashort peptides and collagen fibers [20]. Inspired by these findings, we investigated the NLO properties of our hexamer peptide, LK6. Based on the non-linearity of the intrinsic peptide bonds, we hypotheses that our hexamer peptide, like collagen (which could be viewed as GX1X2, with X1 and X2 corresponding mainly to proline and hydroxyproline), should be able to generate SHG signals.

Figure 1:
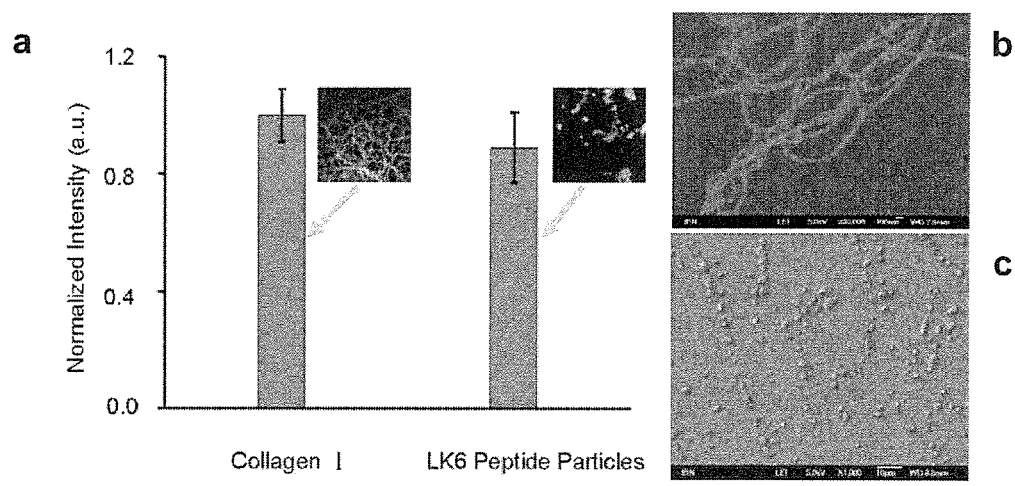
FIG. 1: Fine structure and SHG activity of collagen and amyloid-like peptides.

Peptide particles were prepared by solvent evaporation. Phosphate buffered saline (PBS) was chosen as the solvent. After vacuum drying, the various sizes and shapes of peptide particles were formed (FE-SEM image, FIG. 1c). The particle size was ranging from submicron to 10 microns and the particle shape was irregular. Peptide particles also tended to form larger aggregates during drying (FIG. 2d, FIG. 1a inset and FIG. 4b). Currently, we are manipulating preparation parameters to achieve better control over the size and the shape of peptide particles.

To test our hypothesis, we directly examined LK6 peptide particles using SHG imaging. The SHG signal from LK6 peptide particles was strong and spectrally well defined (FIG. 2a). Illuminating the LK6 peptide particles at 810 nm with a conventional two-photon microscope yielded an SHG signal profile with a discrete peak at 405 nm.

SHG image (green) of LK6 peptide particles was shown in FIG. 1a (inset). LK6 peptide particles showed bright SHG signals. The size and shape of particles can be visualized, consistent with FE-SEM image (FIG. 1a). We then examined the excitation wavelength tunability of SHG signals from these peptide particles. As shown in FIG. 2b, the exciting wavelength was increased from 810 to 890 nm in a conventional two-photon laser-scanning microscopy, the wavelength of the SHG signals from the LK6 peptide particles increased from 405 to 450 nm respectively. Excitation wavelength tunability is one of the advantages of SHG. This enables us freely tune the excitation wavelength to best match the optical properties of the sample.

Biological samples, such as cells and tissues, are known to have auto-fluorescence. With the excitation wavelength tunability, we can avoid auto-fluorescence. In addition, we can further increase penetration depth in tissues by simply increasing excitation wavelength. FIG. 2c shows the emission wavelength data of the SHG signal ($\lambda$ex=850 nm). The data in the graph were fitted to a Gaussian curve exhibiting a maximum at 425 nm, which is exactly half the excitation wavelength of 850 nm. The full width at half-maximum of Gaussian distribution (~10 nm) obeys a relationship to the corresponding wavelength profile of the fundamental beam (~15 nm). Moreover, the dependence of the output signal on irradiation intensity was measured by varying the 850 nm excitation intensity. The linear regression was applied to the log-log plots revealed a quadratic power dependence of SHG intensity to the power intensity, as shown in the FIG. 2d.

$$\log [I425]=0.45+2.01*\log [I850]$$

This confirms the two-photon nature of the emission from LK6 ultrashort peptide particles.

As mentioned previously, collagen fibres produce much stronger SHG signals compared to their building blocks (ten thousand times higher). It is interesting to compare our hexamers to endogenous collagen in terms of SHG signal intensity. In this case, we chose the normal capsular region of rat liver. From in vivo imaging, we observed bright SHG signals from its collagen (FIG. 1a, left inset). Interestingly, our hexamer shows similar intensity to that of collagen (FIG. 1a). This suggested that our hexamer can be used as SHG probes for bioimaging.

In order to use LK6 for bioimaging applications, such as monitoring cells and in vivo imaging, we assessed the cytotoxicity of LK6 by the MTS test. The MTS test was applied to two human cell lines, HeLa and primary human dermal fibroblasts (HDF). The toxicity of LK6 was measured at 0.1, 1, 10, 100 and 1000 μg/mL. Cells were exposed to cell culture media containing LK6 solution for 48 h. Cell viability is reported in FIG. 7a. Cell viability at various LK6 concentrations was either equivalent to or even higher than that of untreated cells over the whole concentration range which was tested in this study (0.1 to 1000 μg/mL). To further confirm these results, we stained cells with and without peptide treatment with solutions containing a mixture of calcein AM and ethidium homodimer-1 (EthD-1). Calcein AM can penetrate cell membrane and be converted to cell membrane impermeable green fluorescent calcein, while red fluorescent EthD-1 is excluded by the intact cell membrane of live cells. FIG. 7b shows the representative live/dead images of cells in response to LK6 solutions (1 and 1000 μg/mL). LK6 shows no toxicity to both HDF and HeLa cells, in agreement with results of MTS assays.

Biological Application

The ability to manufacture SH probes entirely out of LK6 peptides offers additional opportunities as they are biocompatible, biodegradable. A possible application for all-protein/peptide spectra elements such as LK6 is to use them within biological tissues to provide exogenous spectral signatures. These structures can be visualized as all-peptide based contract agents that do not require dyes or chemicals. This is validated by performing an ex vivo experiment in which LK6 peptides are placed under slices of rat fat tissues (FIG. 4a). Peptide particles (green, FIG. 4b) can still be seen clearly as a laser penetrates the tissue. This is a proof of the concept for using LK6 as exogenous SH probes for bioimaging.

As our ultrashort peptides show striking similar to collagen (an extracellular matrix protein, SHG-active molecule and fibrous structures), we can study the interaction between cells and these ultrashort peptides using SHG imaging. Many fundamental biological processes including cell adhesion, migration and differentiation on these ultrashort peptides made matrices can be directly visualized by SHG. The three-dimensional architecture of the tissue engineering scaffolds made of these ultrashort peptides can be viewed in situ and without labelling. The degradation of these scaffolds can be monitored and traced. It also opens the possibility to study the interaction between scaffolds and seeded cells in vitro prior implantation, as well as to monitor the interplay between the scaffolds with the surrounding native tissue in vivo.

In conclusion, we demonstrated that our hexamer peptide, LK6 shows strong SHG signals, similar to those of endogenous normal capsule collagen of rat liver. This ultrashort peptide is biocompatible and biodegradable, which makes it attractive as a future candidate of SH probe for bioimaging.

Further Preferred Embodiments

Abstract

Amyloid-like peptides are an ideal model system to study the mechanisms of amyloidosis which may lead to many human diseases, such as Alzheimer's. Recently, amyloid-like peptides were also used as a new type of biomaterials as tissue engineering scaffolds and drug delivery vehicles. Here we report that these amyloid-like peptides show strong second harmonic generation (SHG) effect, signals equivalent to or even higher than those of endogenous collagen fibers. Several amyloid-like peptides (both synthetic and natural) were examined under SHG microscopy and shown they are SHG-active. These peptides can also be viewed under thick fat tissues (ex vivo) and inside cells (in vitro). This interesting property makes these amyloid-like peptides second harmonic probes for bioimaging applications. Furthermore, SHG microscopy provides us a simple and label-free approach to detect amyloidosis. Lattice corneal dystrophy (LCD) was chosen as a model disease of amyloidosis. Both normal and diseased human corneal biopsy samples were examined under SHG microscopy. Morphological difference between these two can be easily recognized without adequate medical knowledge. Therefore, SHG can be a useful tool for disease diagnosis.

Amyloidosis is responsible for more than fifty human diseases, including Alzheimer's disease (AD), Parkinson's disease (PD), type II diabetes, cataracts and lattice corneal dystrophy (LCD). Inhibition of amyloidosis is a promising strategy for the development of therapeutic agents to treat such diseases. Better understanding of amyloidosis mechanisms may avoid using a trial and error method in searching for amyloid inhibitors, eventually designing or even predicting molecules with inhibitory effects to amyloids. However, the mechanism of amyloidosis is still largely unclear. One logical mechanistic approach is to study how these amyloid-like peptides/proteins fold or misfold [29]. Ultrashort peptides with only three to seven amino acids provide us an ideal model system for mechanistic studies. For example, GGVVIA (GA$_6$) (SEQ ID NO: 100) and KLVF-FAE (KE$_7$) (SEQ ID NO: 99), can self-assemble into amyloid-like aggregates [30, 31]. These two peptides are also known as the core sequence of amyloid-β (Aβ). Aβ is the major component in the amyloid aggregates responsible for AD. Besides ultrashort peptides that can be found in natural peptides/proteins, several designed synthetic ultrashort peptides, such as IVD (ID$_3$) and LIVAGD (LD$_6$) (SEQ ID NO: 19), have shown similar behavior [31, 17]. Both these natural and synthetic peptides are amyloid-like peptides. They all form cross-β peptide structure at molecular level. Morphologically they are usually micrometers in length but only 7-10 nm in diameter [32]. Mechanically they are rigid, with strength comparable to steel [33]. Ultrashort amyloid-like peptides can be not only useful for searching amyloid inhibitors [17], but also as a new type of biomaterials with desirable properties such as biocompatibility and biological activities [31, 34].

Here we report that ultrashort amyloid-like peptides exhibit strong SHG effect. SHG is a nonlinear optical (NLO) effect, first demonstrated in 1961 [35]. Recently, microscopy based on SHG effect has emerged as a powerful bioimaging technique [4]. It provides many significant advantages over the conventional fluorescence imaging techniques for its deeper optical penetration, lower photo-damage and longer observation time [4, 1]. Several amyloid-like peptides (both synthetic and natural), examined under SHG microscopy, revealed they are SHG-active. This interesting property makes these amyloid-like peptides second harmonic probes for bioimaging applications. Furthermore, SHG microscopy provides a simple and label-free approach to detect amyloid-like peptides, which can be a useful tool for disease diagnosis, especially for LCD.

For further details, see Example.

Key Features of the Invention

A novel class of peptides, which only consists of 3-7 amino acids, possesses non-linear optical properties, which can be viewed under second harmonic generation (SHG) microscopy.

An interesting mechanism of self-assembly into fibrous scaffolds, which resembles the collagen fiber in extracellular matrix. Based on the non-linearity of the intrinsic peptide bonds, such supramolecular assembly can generate second harmonic signals Peptide particles demonstrate the SHG excitation wavelength tunability. When the exciting wavelength was increased from 810 to 890 nm in a conventional two-photon laser-scanning microscopy, the wavelength of the SHG signals from the LK6 peptide particles increased from 405 to 450 nm respectively.

Peptide particles demonstrate the two-photon nature of the emission. The emission was fitted nicely to a Gaussian curve and the SHG output signal obeyed a quadratic power dependence of SHG intensity to the power intensity.

Peptide particles generate strong SHG signals, similar as that of endogenous collagen. This suggested that this class of peptides could be used as SHG probes for bioimaging.

The peptides are biocompatible and biodegradable. No toxic effects of these peptides were detected by MTS assay and live/dead staining.

All-peptide based contract agents can be visualized under SHG microscope without additional dyes or chemicals. Therefore, these peptides can be used for monitoring cells and in vivo imaging.

Peptide-based tissue engineering scaffolds can be directly visualized under SHG microscope. Fundamental biological processes including cell adhesion, migration and differentiation on these peptides made matrices can be revealed.

Visualization of peptide aggregation can be used for disease diagnostics. Diseases include Alzheimer's and Parkinson's disease.

Peptides can be easily functionalized to introduce additional functions. Peptide particles can be used as drug or gene delivery vehicles. Peptide-based nanowires can be used as biosenors.

Examples

1. Materials and Methods
1.1 SHG Imaging:

We acquired SHG images using a commercial laser scanning microscopic imaging system (Zeiss LSM 510 META, Jena, Germany) coupled to a mode-locked femtosecond Ti: sapphire laser (Mai-Tai broadband, Spectra-Physics), tunable from 710 nm to 990 nm. To achieve spectral analysis and detect the SHG signal, we used the META detector with 32-gated photon counting module.

1.2 Ultrashort Amyloid-Like Peptides:

We purchased peptides from the American Peptide Company (purity ≥95%). The peptide sequences were confirmed by liquid chromatography-mass spectrometry (LC-MS). Net peptide content varied between 70% and 85%. All peptides were acetylated at the N terminus. Peptide handling and hydrogel preparation were done as reported previously [17].

1.3 Peptide Particles:

We prepared peptide particles by hydrodynamic focusing. Details can be found in elsewhere [21]. The particle size was determined by scanning electron microscopy, showing a grain size of around 5 μm (FIG. 4S).

1.4 Cell Culture:

We cultured both HeLa and human dermal fibroblasts in DMEM supplemented with 10% fetal bovine serum and 1% penicillin/streptomycin (Life technologies, Singapore).

1.5 Human Corneal Biopsy Samples:

Singapore General Hospital provided biopsy samples. The normal tissue was from a seventy-eight year-old Caucasian male. The diseased tissue was from a sixty-year-old female who has lattice corneal dystrophy (LCD).

2. Results and Discussion
2.1 A Hexamer Peptide is Collagen-Like and SHG-Active.

To test whether the amyloid-like peptides of the present invention are SHG-active, we first investigated a hexamer peptide, Ac-LIVAGK-NH$_2$, (LK$_6$) (SEQ ID NO: 27). Peptide particles deposited on a glass microscope slide were examined under an SHG imaging system. Instrument details can be found in our previous work [3]. During the whole experiments, only the backscattered geometry was employed because it is the only suitable configuration for in vivo imaging [1]. We chose collagen I as a control. For more than a decade it has been shown that SHG microscopy can visualize supramolecular assembly of collagen in tissues [1]. Both collagen I and peptide particles showed SHG signals with comparable intensity (FIG. 1a). The fine structures of collagen and peptide particles can be clearly seen under SHG and scanning electron microscopy (SEM, FIG. 1a insert, 1b and 1c).

We further characterized $LK_6$ peptide. It exhibits typical SHG characteristics (FIG. 2). When excited at 810 nm, $LK_6$ emitted a sharp SHG peak at 405 nm (FIG. 2a). We then examined the excitation wavelength tunability of SHG signals from $LK_6$ peptide. In FIG. 2b, as the excitation wavelength was increased from 810 to 890 nm, the wavelength of the SHG signals from the $LK_6$ peptide particles increased from 405 to 445 nm respectively. Biological samples, such as cells and tissues, are known to have auto-fluorescence. With excitation wavelength tunability, we can better avoid auto-fluorescence. In addition, we can further increase penetration depth in tissues by simply increasing excitation wavelength. FIG. 2c shows the emission wavelength data of the SHG signal ($\lambda_{ex}$=850 nm). The data in the graph were fitted to a Gaussian curve exhibiting a maximum at 425 nm, which is exactly half the excitation wavelength of 850 nm. The band width (full width at half-maximum of Gaussian distribution, FWHM) was narrow (~10 nm) and it obeys a relationship to the corresponding wavelength profile of the fundamental beam (~15 nm). Moreover, we measured the dependence of the output signal on irradiation intensity by varying the 850 nm excitation intensity. The linear regression, applied to the log-log plots, revealed a quadratic power dependence of SHG intensity to power intensity, as shown in the FIG. 2d.

$$\log [I_{425}] = 0.45 + 2.01 \times \log [I_{850}] \quad (1)$$

The intensity of SHG signal is proportional to the square of the incident laser intensity. This confirmed the two-photon nature of the emission from $LK_6$ peptide.

2.2 Comparison of Synthetic and Natural Amyloid-Like Peptides Under SHG Microscopy Next, we examined several other amyloid-like peptides, including both natural amyloidogenic core sequences ($NL_6$, $DF_5$, $GA_6$, and $KE_7$) and designed synthetic peptides ($LD_6$, $IS_6$ and $IK_3$). The peptide sequences are listed in Table 1.

TABLE 1

Powder SHG Efficiencies of Various Amyloid-like Peptides and Human Collagen Subtypes.

| Amyloid-like Peptides/ Human Collagens | SEQ ID NO. | $I^{2\omega}/I^{2\omega}(\text{sucrose})^{a)}$ |
|---|---|---|
| IVK ($IK_3$) |  | 3.31 ± 0.57 |
| LIVAGD ($LD_6$) | 19 | 3.06 ± 0.65 |
| ILVAGS ($IS_6$) | 98 | 1.96 ± 0.58 |
| LIVAGK ($LK_6$) | 27 | 0.95 ± 0.19 |
| KLVFFAE ($KE_7$) | 99 | 3.18 ± 0.67 |
| GGVVIA ($GA_6$) | 100 | 1.52 ± 0.43 |
| DFNKF ($DF_5$) | 101 | 0.89 ± 0.33 |
| NFGAIL ($NL_6$) | 102 | 0.76 ± 0.21 |
| Type I |  | 1.23 ± 0.36 |
| Type II |  | 0.41 ± 0.13 |
| Type III |  | N.D.$^{b)}$ |
| Type IV |  | N.D.$^{b)}$ |
| Type V |  | N.D.$^{b)}$ |

$^{a)}$Value = Average ± standard deviation;
$^{b)}$N.D. = not detected.

All these peptides are SHG-active. We used a powder technique developed by Kurtz and Perry [22] to evaluate the SHG efficiency of these second-order nonlinear optical materials. Sucrose, having a relatively modest nonlinearity, was chosen as a standard to evaluate second harmonic generation efficiencies [23]. In Table 1, all amyloid-like peptides that have been tested showed higher or equivalent SHG efficiency compared to sucrose. The efficiency of $LD_6$ and $IK_3$ were even three times higher than that of sucrose. These may due to their molecular structures. $LD_6$ is known to form hydrogel at much lower concentrations compared to $LK_6$. The trimer $IK_3$ has larger dipole moment compared to $LK_6$. Human collagen subtypes I to V were examined (also listed in Table 1). Only type I and II showed SHG activity, III, IV and V did not. This agrees with the previous findings [4, 24]. In Table 1, all the tested amyloid-like peptides were SHG-active with some showing even higher SHG efficiency than collagen subtypes. This provides a broad spectrum of materials as second harmonic probes.

We have previously showed that $NL_6$, $DF_5$, $GA_6$, and $KE_7$ as well as $LD_6$, $IS_6$, $LK_6$ and $IK_3$ self-assembled into hydrogels at 12 mM [18]. However, in this study, the gelation speed does not correlate to that of SHG efficiency (data not shown). We chose three rational designed hexamers, $LD_6$ (negatively charged), $IS_6$ (neutral) and $LK_6$ (positively charged) to investigate the effect of the charged head groups. The SHG efficiency of these three hexamers followed the order of $LD_6 > IS_6 > LK_6$.

We also investigate the effect of the peptide chain length by choosing $IK_3$, a trimer, compared to the other three hexamers. It followed the order of $IK_3$ (trimer) > $LD_6$ (hexamer). Both findings are helpful for designing a superior amyloid-like peptide.

We then investigated the SHG efficiency of four natural amyloidogenic core sequences. They followed the order of $KE_7 > GA_6 > DF_5 > NL_6$ (Table 1 and FIG. 6). $KE_7$ (KLVF-FAE) (SEQ ID NO: 99), containing its diphenylalanine (FF) motif, showed the highest SHG efficiency among these four peptides. However, its SHG efficiency is similar as that of $IK_3$. It is noteworthy that $IK_3$ is an aliphatic peptide. Aromatic residues such as tyrosine and tryptophan are known to be used as an endogenous molecular probe of peptides and proteins for SHG at the air-water interface [25]. However, our results indicated that aromatic residues are not necessary for higher SHG efficiency. $LD_6$, $IS_6$, $LK_6$ and $IK_3$ are all aliphatic and lacking aromatic residues, clearly makes them a unique type of peptides for SHG applications. These peptides are rational designed by Hauser and colleagues [17, 20]. They are amphiphilic, consisting of an aliphatic amino acid tail of decreasing hydrophobicity and a hydrophilic head. They can self-assembly via parallel-antiparallel α-helical pairs and subsequent stacking into β-turn fibrils, which show striking similarity to collagen fibers [20].

We reason that the origin of these amyloid-like peptides' SHG activity comes from their nanostructures. A recent study showed that the origin of SHG signals from collagen fibers possibly lies in their peptide bonds [19]. The collagen fiber building blocks were mimicked by tri-amino acid peptides PPG and GGG (P and G are the one letter code for Proline and Glycine respectively).

In addition, a molecular-level property of the nonlinearity, i.e., the first hyperpolarizability, β, was measured by Hyper Rayleigh Scattering (HRS). The first hyperpolarizability of these trimers was about $0.087 \times 10^{-30}$ esu (esu is the unit of the first hyperpolarizability) [19]. However, the first hyperpolarizability of collagen I was found to be $(1250 \pm 20) \times 10^{-30}$ esu [19], which could be viewed as ten thousand trimers combining together. Based on the non-linearity of the intrinsic peptide bonds and their aggregation capability, these amyloid-like peptides can generate SHG signals, just like collagen.

2.3 Cytocompatibility of a Hexamer Peptide

In order to use $LK_6$ for bioimaging applications, such as in vitro monitoring cells and in vivo imaging the whole animal, we assessed the cytotoxicity of $LK_6$ by the MTS test and live/dead assay with two human cell lines, human epithelial carcinoma cells (HeLa) and primary human dermal fibroblasts (HDF). Cell viability and the representative live/dead images of cells in response to $LK_6$ solutions was reported in FIG. 7. $LK_6$ shows no toxicity to either HDF or HeLa cells.

2.4 A Hexamer Peptide as a Second Harmonic Probe for In Vitro Cell Imaging

A possible application for $LK_6$ is cell imaging. To this end, HeLa cells were incubated with biotin-conjugated $LK_6$ for 4 h and then fixed for immunostaining. $LK_6$ peptides were visualized by both SHG and confocal fluorescence microscopes. In FIG. 3, biotin-conjugated peptides displayed green color as we added DyLight™ 488-conjugated NeutrAvidin™ (Thermo Scientific, Singapore). Meanwhile, peptides can be detected under SHG, displaying pseudored color.

2.5 A Hexamer Peptide as a Second Harmonic Probe for Ex Vivo Deep Imaging

Another possible application for $LK_6$ is to use them within biological tissues to provide exogenous SHG signatures. These structures can be envisioned without any dyes or chemicals, even in a highly scattering environment such as living tissue. This is validated by performing an ex vivo experiment in which $LK_6$ peptide samples are placed under a slice of fat tissue (great omentum removed from a sacrificed rat, thickness~50 μm). The results are shown in FIG. 4 and confirm the ability to detect SHG signals under sub-millimeter thick tissue.

2.6 Diseased and Normal Human Corneal Biopsy Samples Examined by SHG Microscopy

More interestingly, when we examined the human corneal biopsy samples (FIGS. 5a and 5b), both amyloids (indicated by arrow) and collagen can be seen. Under SHG, the normal corneal sample showed collagen fibrils aligned as parallel straight lines in stroma. By contrast diseased samples showed collagen fibrils became curved and thicker. The thickened collagen fibrils could be due to amyloid deposits. Thus, SHG provides us a new diagnostic tool for lattice corneal dystrophy (LCD) that is superior to the existing histological staining methods: SHG is label-free (no staining such as Congo red is required).

2.7 Other Applications

In our laboratory, we have explored the biomedical applications of ultrashort amyloid-like peptides in many aspects. In one study, an anti-cancer drug, oxaliplatin, was tagged to our peptides by click chemistry [26]. Peptides were then injected into mice tumor sites. In vivo studies showed significant tumor growth inhibition. In another study, we used ultrashort peptides as a wound dressing. It heals the burn wounds much faster in a rat model [27]. Because our peptides are SHG-active, we can visualize these processes with SHG microscopy when we apply our peptides as drug delivery vehicles or wound dressings. Click chemistry enables adding therapeutic molecules to the ultrashort peptides. Thus, ultrashort peptides can also be used as theranostic agents that provide imaging and therapy at the same time. Recently, SHG microendoscopy has been developed [28]. Therefore, we could expect for more bioimaging applications by using amyloid-like peptides as a second harmonic probe.

CONCLUSION

We demonstrated for the first time that amyloid-like peptides are nonlinear optical materials showing strong SHG signals. Amyloid-like peptides can be viewed under thick fat tissues and inside cells which make them suitable as second harmonic probes. Amyloid-like peptide nanomaterials hold great potential in nanotechnology and nanomedicine. Their nonlinear optical properties hold promise for new bioimaging applications.

It is to be understood that the described embodiment(s) have been provided only by way of exemplification of this invention, and that further modifications and improvements thereto, as would be apparent to persons skilled in the relevant art, are deemed to fall within the broad scope and ambit of the present invention described herein.

REFERENCES

1. Campagnola P J, Loew L M, Second-harmonic imaging microscopy for visualizing biomolecular arrays in cells, tissues and organisms. Nat. Biotechnol. 2003; 21: 1356-60.
2. Bayan C., Levitt J M, Miller E, Kaplan D, Georgakoudi I, Fully automated, quantitative, noninvasive assessment of collagen fiber content and organization in thick collagen gels. J. Appl. Phy. 2009; 105: 102042.
3. Zhuo S M, Chen J X, Wu G Z, Xie S S, Zheng L Q, Jiang X S, Zhu X Q, Quantitatively linking collagen alteration and epithelial tumor progression by second harmonic generation microscopy. Appl. Phys. Lett. 2010; 96: 213704.
4. Chen X, Nadiarynkh O, Plotniko S, Campagnola P J, Second harmonic generation microscopy for quantitative analysis of collagen fibrillar structure. Nat. Protoc. 2012; 7: 654-69.
5. Appel A A, Anastasio M A, Larson J C, Brey E M, Imaging challenges in biomaterials and tissue engineering. Biomaterials 2013; 34: 6615-30.
6. Brackmann C, Zaborowska M, Sundberg J, Gatenholm P, Enejder A, In situ imaging of collagen synthesis by osteoprogenitor cells in microporous bacterial cellulose scaffolds. Tissue Eng Part C Methods, 2012; 18: 227-34.
7. Schenke-Layland K, Non-invasive multiphoton imaging of extracellular matrix structures. J Biophotonics, 2008; 1: 451-62.
8. Staedler D, Magouroux T, Hadji R, Joulaud C, Extermann J, Schwungi S, Passemard S, Kasparian C, Clarke G, Gerrmann M, Le Dantec R, Mugnier Y, Rytz D, Ciepielewski D, Galez C, Gerber-Lemaire S, Juillerat-Jeanneret L, Bonacina L, Wolf J P, Harmonic nanocrystals for biolabeling: A survey of optical properties and biocompatibility. ACS Nano 2012; 6: 2542-9.
9. Tong L, Cheng J-X, Label-free imaging through nonlinear optical signals—Review article. Material Today, 2011; 14: 264-73.
10. Cox G, Kable E, Jones A, Fraser I, Manconi F, Gorrell M D, 3-Dimensional imaging of collagen using second harmonic generation. J. Struct. Biol. 2003; 141: 53-62.
11. Rosenman G, Beker P, Koren I, Yevnin M, Bank-Srour B, Mishina E, Semin S, Bioinspired peptide nanotubes: deposition technology, basic physics and nanotechnology applications. J. Pept. Sci. 2011; 17: 75-87.
12. Campagnola P, Second harmonic generation imaging microscopy: Applications to diseases diagnostics. Anal. Chem. 2011; 83: 3224-31.
13. Pantazis P, Maloney J, Wu D, Fraser S E, Second harmonic generating (SHG) nanoprobes for in vivo imaging. PNAS, 2010; 107: 14535-40.
14. Bonacina L., Harmonic particles toward targeted diagnosis and therapy. Mol. Pharmaceutics 2013; 10: 783-92.
15. Xia T, Kovochich M, Liong M, Ma☐dler L, Gilbert B, Shi H, Yeh J I, Zink J I, Nel A E, Comparison of the mechanism of toxicity of zinc oxide and cerium oxide 16. Klaine S J, Alvarez P J J, Batley G E, Fernandes T F, Handy R D, Lyon D Y, Mahendra S, McLaughlin M J, Lead J R, Nanomaterials in the environment: Behavior, fate, bioavailability, and effects. Environ. Toxicol. Chem. 2008; 27: 1825-51.
17. Hauser C A E, Deng R, Mishra A, Loo Y, Khoe U, Zhuang F, Cheong D W Accardo A, Sullivan M B, Riekel C, Ying J Y, Hauser U A, Natural tri- to hexapeptides self-assemble in water to amyloid beta-type fiber aggregates by unexpected alpha-helical intermediate structures. PNAS 2011; 108: 1361-6.
18. Lakshmanan A, Cheong D W, Accardo A, Di Fabrizio E, Riekel C, Hauser C A E, Aliphatic peptides show similar self-assembly to amyloid core sequences, challenging the importance of aromatic interactions in amyloidosis. PNAS 2013; 110:519-24.
19. Duboisset J, Deniset-Besseau A, Benichou E, Russier-Antoine I, Lascoux N, Jonin C, Hache F, Schanne-Klein M.-C, Brevet P-F, A bottom-up approach to build the hyperpolarizability of peptides and proteins from their amino acids. *J. Phys. Chem. B* 2013; 117: 9877-81.
20. Mishra A, Loo Y H, Deng R, Chuah Y J, Hee H T, Ying J Y, Hauser C A E, Ultrasmall natural peptides self-assemble to strong temperature-resistant helical fibers in scaffolds suitable for tissue engineering. Nano Today 2011; 6: 232-9.
21. Tresset, G., Marculescu, C., Salonen, A., Ni, M. & Iliescu, C. Fine Control Over the Size of Surfactant—Polyelectrolyte Nanoparticles by Hydrodynamic Flow Focusing. *Anal. Chem.* 85, 5850-5856, (2013).
22. Kurtz, S. K. & Perry, T. T. A POWDER TECHNIQUE FOR EVALUATION OF NONLINEAR OPTICAL MATERIALS. *Journal of Applied Physics* 39, 3798-&, (1968).
23. Bourhill, G. et al. Powder second harmonic generation efficiencies of saccharide materials. *Chem. Mater,* 5, 802-808, (1993).
24. Su, P. J. et al. The discrimination of type I and type II collagen and the label-free imaging of engineered cartilage tissue. *BIOMATERIALS* 31, 9415-9421, (2010).
25. Nasir, M. N. et al. Influence of the tyrosine environment on the second harmonic generation of iturinic antimicrobial lipopeptides at the air-water interface *Physical Chemistry Chemical Physics* 15, 19919-19924, (2013).
26. Reithofer, M. R. et al. Ligation of anti-cancer drugs to self-assembling ultrashort peptides by click chemistry for localized therapy. *Chemical Science* 5, 625-630, (2014).
27. Loo, Y. et al. Ultrashort peptide nanofibrous hydrogels for the acceleration of healing of burn wounds. *BIOMATERIALS* 35, 4805-4814, (2014).
28. Zhang, Y. et al. A compact fiber-optic SHG scanning endomicroscope and its application to visualize cervical remodeling during pregnancy. *PNAS* 109, 12878-12883, (2012).
29. Dobson, C. M. Protein folding and misfolding. *Nature* 426, 884-890, (2003).
30. Kirschner, D. A. et al. Synthetic peptide homologous to beta protein from Alzheimer disease forms amyloid-like fibrils in vitro. *PNAS* 84, 6953-6957, (1987).
31. Hauser, C. A., Maurer-Stroh, S. & Martins, I. C. Amyloid-based nanosensors and nanodevices. *Chem Soc Rev*, (2014).
32. Shirahama, T. & Cohen, A. S. HIGH-RESOLUTION ELECTRON MICROSCOPIC ANALYSIS OF THE AMYLOID FIBRIL. *J Cell Biol* 33, 679-708, (1967).
33. Smith, J. F., Knowles, T. P. J., Dobson, C. M., MacPhee, C. E. & Welland, M. E. Characterization of the nanoscale properties of individual amyloid fibrils. *Proceedings of the National Academy of Sciences of the United States of America* 103, 15806-15811, (2006).
34. Wu, E. C., Zhang, S. & Hauser, C. A. E. Self-Assembling Peptides as Cell-Interactive Scaffolds. *Adv. Funct. Mater.*, n/a-n/a, (2011).
35. Franken, P. A., Hill, A. E., Peters, C. W. & Weinreich, G. Generation of Optical Harmonics. *Physical Review Letters* 7, 118-119, (1961).

The invention claimed is:
1. A second harmonic generation (SHG) microscopy method for imaging a sample, the method comprising:
   (a) contacting with a sample or a tissue a non-linear optical material that comprises peptides and/or peptidomimetics having the general Formula I:

$Z_a\text{-}(X)_b\text{-}(Y)_c\text{-}Z'_d$  (I)

wherein
   Z is an N-terminal protecting group;
   a is 0 or 1;
   X is, at each occurrence, independently selected from the group consisting of aliphatic amino acids and aliphatic amino acid derivatives, and wherein the overall hydrophobicity decreases from N- to C-terminus;
   b is an integer selected from 1 to 7;
   Y is selected from the group consisting of polar amino acids and polar amino acid derivatives;
   c is 1 or 2;
   Z' is a C-terminal protecting group; and
   d is 0 or 1,
   and b+c is at least 2; and
   (b) imaging the sample or tissue under a second harmonic generation (SHG) excitation wavelength to produce a SHG signature of the sample or tissue.

2. The method according to claim 1, wherein the non-linear optical material comprises a hydrogel, a fibrous structure, or a peptide particle wherein the hydrogel, or the fibrous structure is formed by dissolving the peptide or peptidomimetic in an aqueous solution or wherein the peptide particle is formed by evaporating the aqueous solution from the hydrogel, or the fibrous structure.

3. The method of claim 2, wherein the at least one peptide or peptidomimetic is dissolved in an aqueous solution at a concentration of 0.01 µg/ml to 100 mg/ml.

4. The method of claim 2, further comprising exposing the peptide or peptidomimetic in aqueous solution to a temperature of 20° C. to 90° C.

5. The method of claim 2, wherein the aqueous buffer comprises phosphate buffered saline (PBS).

6. The method of claim 2, wherein the hydrogel, the fibrous structure or the peptide particle are used:
   (a) as probes for monitoring cells, in vitro and/or in vivo (bio-)imaging, as exogenous SHG probes or as drug or gene delivery vehicles;
   (b) for visualizing peptide-based tissue engineering scaffolds, comprising studying biological processes; or
   (c) as a diagnostic, for the diagnosis of diseases comprising or associated with the aggregation of peptide or protein structures of amyloidosis.

7. The method of claim 1, wherein the aliphatic amino acids and aliphatic amino acid derivatives and the polar amino acids and polar amino acid derivatives are either D-amino acids or L-amino acids.

8. The method of claim 1, wherein the aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G).

9. The method of claim 1, wherein all or a portion of the aliphatic amino acids are arranged in an order of decreasing amino acid size in the direction from N- to C-terminus, wherein the size of the aliphatic amino acids is defined as I=L>V>A>G.

10. The method of claim 1, wherein the aliphatic amino acids have a sequence selected from the group consisting of

| | |
|---|---|
| LIVAG, | (SEQ ID NO: 1) |
| ILVAG, | (SEQ ID NO: 2) |
| ILVAA, | (SEQ ID NO: 3) |
| LIVAA, | (SEQ ID NO: 4) |
| LAVAG, | (SEQ ID NO: 5) |
| IAVAG, | (SEQ ID NO: 6) |
| AIVAG, | (SEQ ID NO: 7) |
| GIVAG, | (SEQ ID NO: 8) |
| VIVAG, | (SEQ ID NO: 9) |
| ALVAG, | (SEQ ID NO: 10) |
| GLVAG, | (SEQ ID NO: 11) |
| VLVAG, | (SEQ ID NO: 12) |
| IVAG, | (SEQ ID NO: 13) |
| LIVA, | (SEQ ID NO: 14) |
| LIVG, | (SEQ ID NO: 15) |
| ILVA, | (SEQ ID NO: 16) |
| ILVG, | (SEQ ID NO: 17) |
| LVAG, | (SEQ ID NO: 18) |
| IVA | |
| IVG, | |
| VIG, | |
| IVA, | |
| VIA, | |
| IV | |
| VI | |
| LIVAGD, | (SEQ ID NO: 19) |
| ILVAGD, | (SEQ ID NO: 20) |
| ILVAAD, | (SEQ ID NO: 21) |
| LIVAAD, | (SEQ ID NO: 22) |

LAVAGD, (SEQ ID NO: 23)

IAVAGD, (SEQ ID NO: 24)

AIVAGD, (SEQ ID NO: 25)

LIVAGE, (SEQ ID NO: 26)

LIVAGK, (SEQ ID NO: 27)

ILVAGK, (SEQ ID NO: 28)

ILVAAK, (SEQ ID NO: 29)

IAVAGK, (SEQ ID NO: 30)

AIVAGK, (SEQ ID NO: 31)

LIVAGT, (SEQ ID NO: 32)

ILVAAT, (SEQ ID NO: 33)

IAVAGT, (SEQ ID NO: 34)

AIVAGT, (SEQ ID NO: 35)

LIVAD, (SEQ ID NO: 36)

LIVGD, (SEQ ID NO: 37)

ILVAD, (SEQ ID NO: 38)

ILVGD, (SEQ ID NO: 39)

LVAGD, (SEQ ID NO: 40)

IVAD, (SEQ ID NO: 41)

IVAK, (SEQ ID NO: 42)

IVGD, (SEQ ID NO: 43)

VIGD, (SEQ ID NO: 44)

IVAD, (SEQ ID NO: 45)

VIAD, (SEQ ID NO: 46)

IVGK, (SEQ ID NO: 47)

VIGK, (SEQ ID NO: 48)

IVAK, (SEQ ID NO: 49)

VIAK, (SEQ ID NO: 50)

IIID, (SEQ ID NO: 51)

IIIK, (SEQ ID NO: 52)

IVD,

IVK,

IID,

LVE,

IVE,

LVD,

VIE,

VID,

VIK,

VLD,

VLE,

LLE,

LLD,

IIE,

ID,

IE,

LIVAGOrn, (SEQ ID NO: 53)

ILVAGOrn, (SEQ ID NO: 54)

ILVAAOrn, (SEQ ID NO: 55)

IAVAGOrn, (SEQ ID NO: 56)

AIVAGOrn, (SEQ ID NO: 57)

LIVAGDab, (SEQ ID NO: 58)

ILVAGDab, (SEQ ID NO: 59)

ILVAADab, (SEQ ID NO: 60)

IAVAGDab, (SEQ ID NO: 61)

AIVAGDab, (SEQ ID NO: 62)

LIVAGDap, (SEQ ID NO: 63)

ILVAGDap, (SEQ ID NO: 64)

ILVAADap, (SEQ ID NO: 65)

IAVAGDap, (SEQ ID NO: 66)

AIVAGDap, (SEQ ID NO: 67)

LIVAOrn, (SEQ ID NO: 68)

LIVGOrn, (SEQ ID NO: 69)

ILVAOrn, (SEQ ID NO: 70)

ILVGOrn, (SEQ ID NO: 71)

LVAGOrn, (SEQ ID NO: 72)

LIVADab, (SEQ ID NO: 73)

LIVGDab, (SEQ ID NO: 74)

ILVADab, (SEQ ID NO: 75)

ILVGDab, (SEQ ID NO: 76)

LVAGDab, (SEQ ID NO: 77)

LIVADap, (SEQ ID NO: 78)

LIVGDap, (SEQ ID NO: 79)

ILVADap, (SEQ ID NO: 80)

ILVGDap, (SEQ ID NO: 81)

LVAGDap, (SEQ ID NO: 82)

IVAOrn, (SEQ ID NO: 83)

IVGOrn, (SEQ ID NO: 84)

VIGOrn, (SEQ ID NO: 85)

IVAOrn, (SEQ ID NO: 86)

VIAOrn, (SEQ ID NO: 87)

IVADab, (SEQ ID NO: 88)

IVGDab, (SEQ ID NO: 89)

VIGDab, (SEQ ID NO: 90)

IVADab, (SEQ ID NO: 91)

VIADab, (SEQ ID NO: 92)

IVADap, (SEQ ID NO: 93)

IVGDap, (SEQ ID NO: 94)

VIGDap, (SEQ ID NO: 95)

IVADap, (SEQ ID NO: 96)

VIADap, (SEQ ID NO: 97)

IVOrn,

IVDab,

IVDap,

VIOrn,

VIDab,

VIDap,
and

ILVAGS. (SEQ ID NO: 98)

11. The method of claim 1, wherein the polar amino acids are selected from the group consisting of aspartic acid (Asp, D), asparagine (Asn, N), glutamic acid (Glu, E), glutamine (Gln, Q), 5-N-ethyl-glutamine (theanine), citrulline, thiocitrulline, cysteine (Cys, C), homocysteine, methionine (Met, M), ethionine, selenomethionine, telluromethionine, threonine (Thr, T), allothreonine, serine (Ser, S), homoserine, arginine (Arg, R), homoarginine, ornithine (Orn), lysine (Lys, K), N(6)-carboxymethyllysine, histidine (His, H), 2,4-diaminobutyric acid (Dab), 2,3-diaminopropionic acid (Dap), and N(6)-carboxymethyllysine.

12. The method of claim 1, wherein $(Y)_c$ has a sequence selected from Asp, Asn, Glu, Gln, Ser, Thr, Cys, Met, Lys, Orn, Dab, His, Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp Thr-Thr, Ser-Ser, Thr-Ser, Ser-Thr, Asp-Ser, Ser-Asp, Ser-Asn, Asn-Ser, Gln-Ser, Ser-Gln, Glu-Ser, Ser-Glu, Asp-Thr, Thr-Asp, Thr-Asn, Asn-Thr, Gln-Thr, Thr-Gln, Glu-Thr, Thr-Glu, Cys-Asp, Cys-Lys, Cys-Ser, Cys-Thr, Cys-Orn, Cys-Dab, Cys-Dap, Lys-Lys, Lys-Ser, Lys-Thr, Lys-Orn, Lys-Dab, Lys-Dap, Ser-Lys, Ser-Orn, Ser-Dab, Ser-Dap, Orn-Lys, Orn-Orn, Orn-Ser, Orn-Thr, Orn-Dab, Orn-Dap, Dab-Lys, Dab-Ser, Dab-Thr, Dab-Orn, Dab-Dab, Dab-Dap, Dap-Lys, Dap-Ser, Dap-Thr, Dap-Orn, Dap-Dab, and Dap-Dap.

13. The method of claim 1, wherein a is 1 and the N-terminal protecting group Z has the general formula —C(O)—R, wherein R is selected from the group consisting of H, unsubstituted or substituted alkyls, and unsubstituted or substituted aryls.

14. The method of claim 1, wherein said N-terminal protecting group Z is an acetyl group, or a peptidomimetic molecule, modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

15. The method of claim 1, wherein the C-terminal protecting group Z' is:
(a) an amide group;
(b) an ester group; or
(c) a peptidomimetic molecule or a natural or synthetic amino acid derivative thereof, the C-terminus of which can be modified with a functional group selected from the group consisting of carboxylic acid, amide, alcohol, aldehyde, amine, imine, nitrile, an urea analog, phosphate, carbonate, sulfate, nitrate, maleimide, vinyl sulfone, azide, alkyne, alkene, carbohydrate, imide, peroxide, ester, aryl, ketone, sulphite, nitrite, phosphonate, and silane.

16. The method of claim 1, wherein the peptide or peptidomimetic comprises at least one additional compound selected from the group consisting of: small molecules, sugars, alcohols, hydroxy acids, amino acids, vitamins, biotin, L-Dopa, thyroxine, bioactive molecules or moieties, growth factors, cytokines, lipids, cell receptor ligands, hormones, prodrugs, drugs, vitamins, antigens, antibodies, antibody fragments, oligonucleotides, DNA, messenger RNA, short hairpin RNA, small interfering RNA, microRNA, peptide nucleic acids, aptamers, saccharides, label(s), dye(s), imaging contrast agents, pathogens, viruses, bacteria and parasites, microparticles, nanoparticles, and combinations thereof,
wherein the at least one additional compound is covalently attached or coupled to the peptide or peptidomimetic, to the C-terminal group Z', amino acid side chain(s) and/or linker,
and wherein the attachment or coupling can be carried out before, during or after self-assembly of the peptide or peptidomimetic.

17. The method of claim 1, wherein the peptide or peptidomimetic is present at a concentration in the range of from 0.1% to 30% (w/w), with respect to the total weight of the hydrogel or fibrous structure.

18. A second harmonic generation (SHG) microscopy method for imaging a sample, the method comprising:
(a) contacting with a sample or a tissue a non-linear optical material that comprises peptides and/or peptidomimetics having the general Formula II:

$$Z_a\text{-M-}Z'_d \qquad (II)$$

wherein
Z is an N-terminal protecting group;
a is 0 or 1;
M is an amino acid sequence selected from SEQ ID NOs: 99 to 102;
Z' is a C-terminal protecting group; and
d is 0 or 1; and
(b) imaging the sample or tissue under a second harmonic generation (SHG) excitation wavelength to produce a SHG signature of the sample or tissue.

19. The method of claim 6, wherein the biological processes are cell adhesion, migration or differentiation.

* * * * *